United States Patent [19]

Burkholder et al.

[11] Patent Number: 5,183,054
[45] Date of Patent: Feb. 2, 1993

[54] ACTUATED BIOPSY CUTTING NEEDLE WITH REMOVABLE STYLET

[75] Inventors: Richard A. Burkholder, St. Peters, Mo.; Gregory G. Acker, Springboro, Pa.

[73] Assignee: Sherwood Medical Company, St. Louis, Mo.

[21] Appl. No.: 756,650

[22] Filed: Sep. 9, 1991

[51] Int. Cl.⁵ ............................................. A61B 10/00
[52] U.S. Cl. .................................... 128/754; 606/171
[58] Field of Search ............... 128/754, 753, 751, 749; 606/167, 168, 170, 172

[56] References Cited

U.S. PATENT DOCUMENTS 4,702,261 10/1987 Cornell et al. ...................... 128/754
4,881,551 11/1989 Taylor ................................. 128/754

Primary Examiner—Max Hindenburg
Assistant Examiner—Guy V. Tucker
Attorney, Agent, or Firm—Andrew J. Beck; Montgomery W. Smith; Curtis D. Kinghorn

[57] ABSTRACT

A biopsy device is disclosed having a tubular cannula through which a stylet having a stylet cavity near the distal end is placed. The stylet is attached to a stylet actuator and the cannula is attached to a cannula actuator. Both actuators are constrained by a housing to relative proximal and distal movement. In use, the stylet and stylet cavity are positioned in the cannula. The cannula and stylet are then inserted into the patient's tissue. When a sample is to be taken, the stylet is moved farther into the patient's tissue thereby exposing the stylet cavity. The patient's tissue then falls into the stylet cavity. Thereafter, the cannula actuator moves the cannula forward over the stylet cavity thereby cutting the tissue so that a sample of the tissue remains in the stylet cavity which becomes encased by the cannula as the cannula is moved forward. The stylet is selectively removable from the cannula and the biopsy device through the housing enclosing the biopsy device so that the tissue sample obtained by the biopsy device may be retrieved while the cannula of the biopsy device remains in place within the patient. Thereafter, the stylet may be reinserted through the housing and cannula into the patient's tissue where additional tissue samples may be obtained. The biopsy device also includes an optional hand grip attached to the device for facilitating one hand operation of the biopsy device.

17 Claims, 12 Drawing Sheets

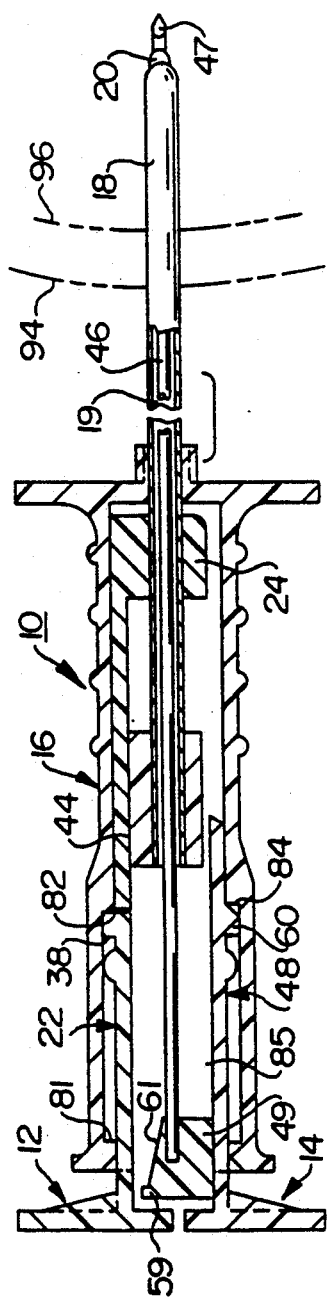
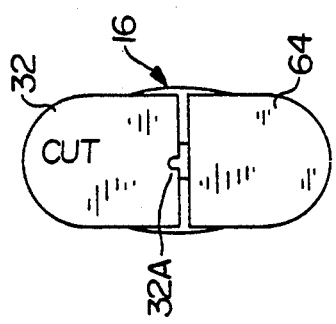
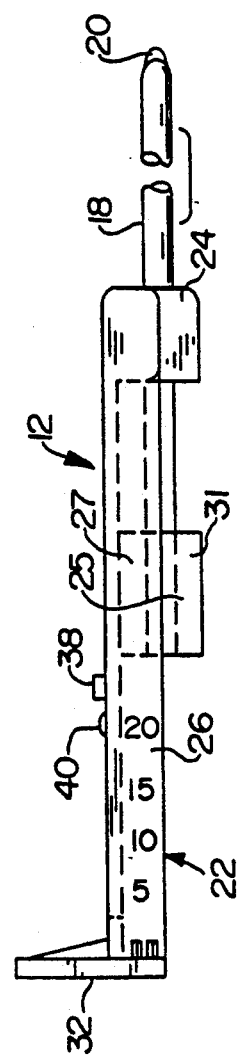
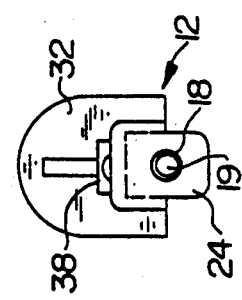
FIG. 3
FIG. 4
FIG. 5
FIG. 6

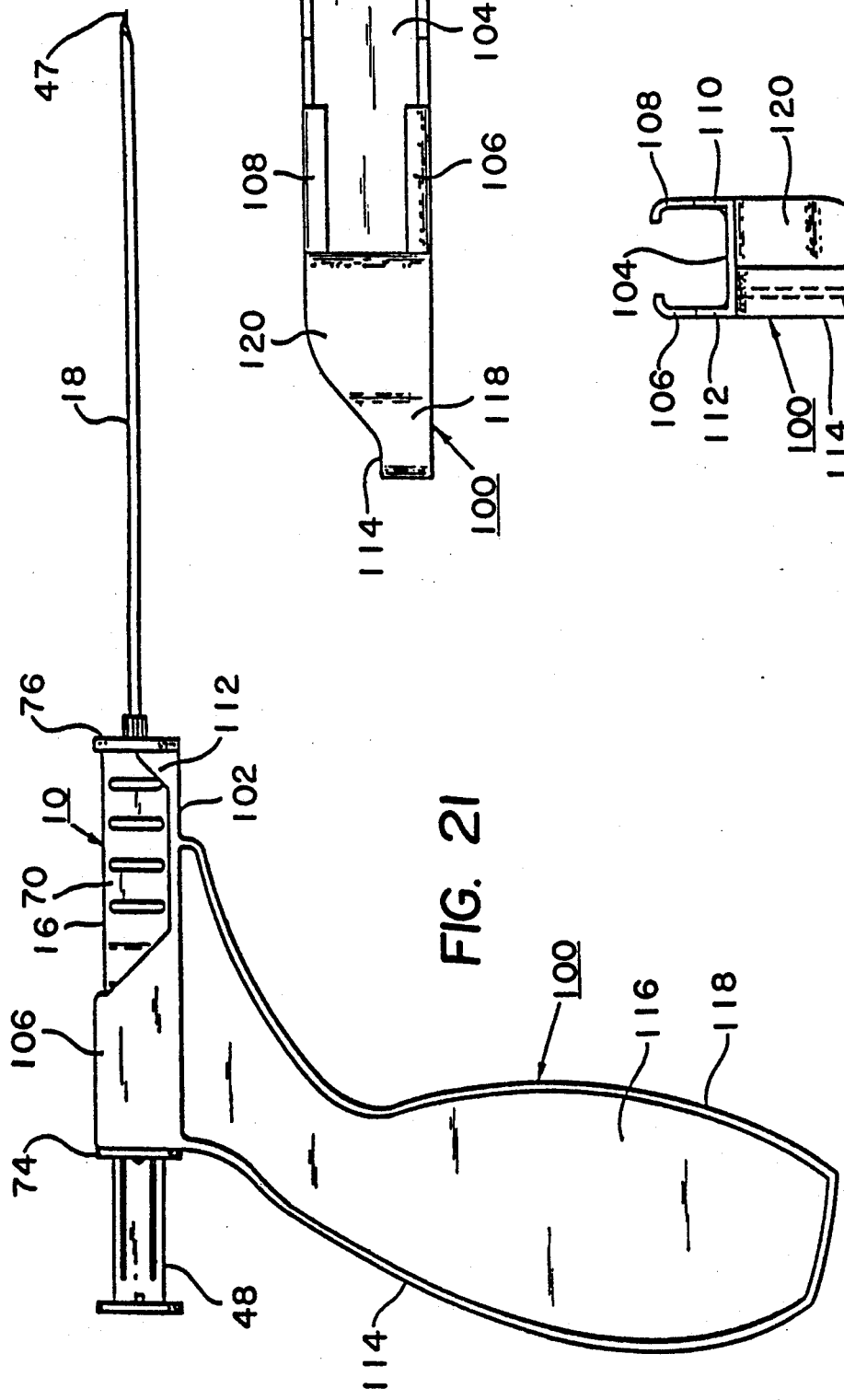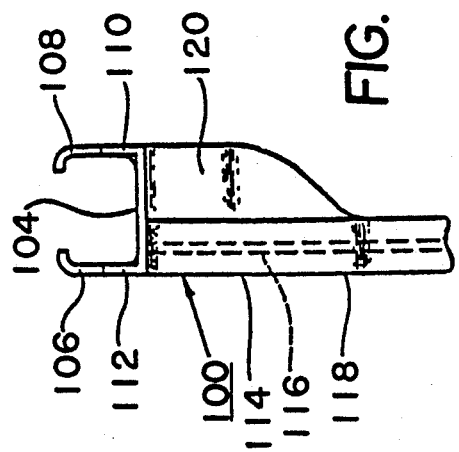

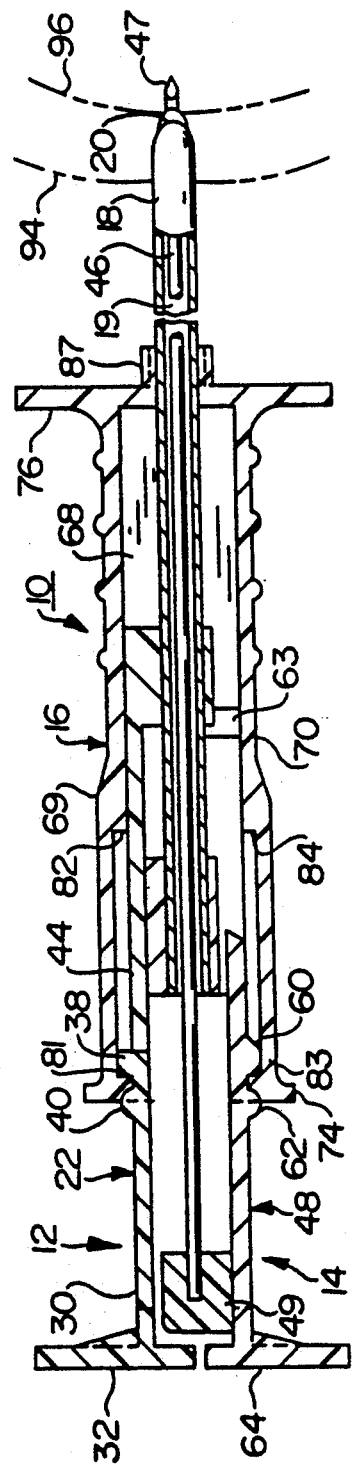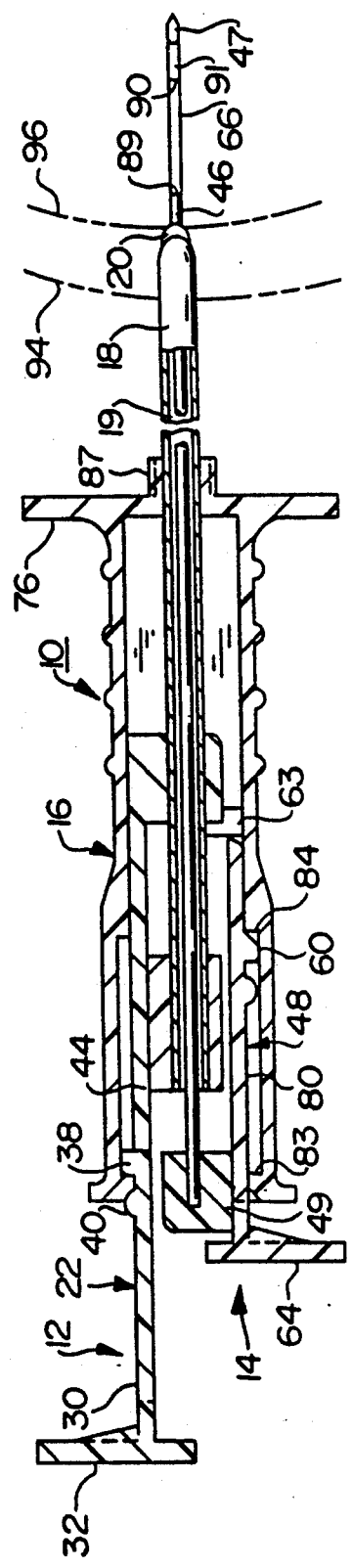
FIG. 26
FIG. 27

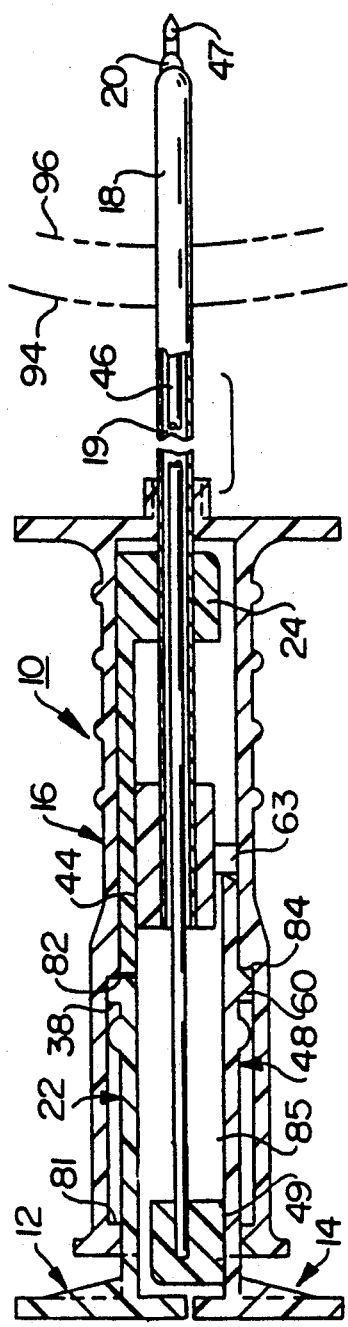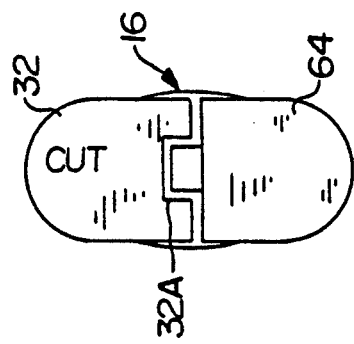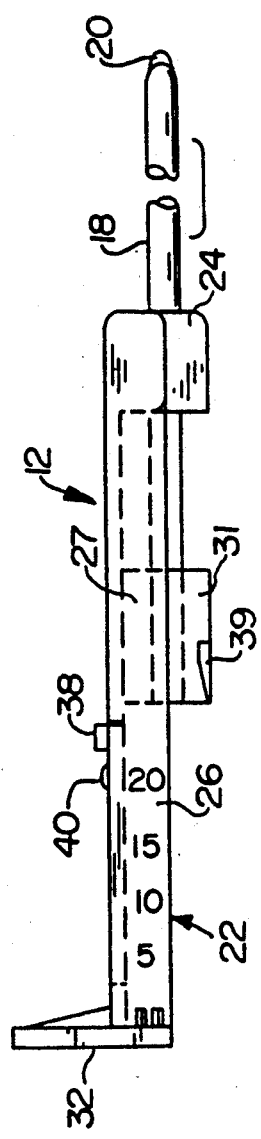
FIG. 28
FIG. 29
FIG. 30

ACTUATED BIOPSY CUTTING NEEDLE WITH REMOVABLE STYLET

TECHNICAL FIELD

This invention relates to biopsy devices and methods of taking biopsies and more particularly to a biopsy device, having a cannula with a removable stylet, capable of effecting repeated subcutaneous biopsies without having to reinsert the cannula of the biopsy device into the patient after each sample is collected.

BACKGROUND

Some biopsy devices include a tubular cutting element or cannula having a body tissue cutting distal end, and a stylet slidable in the cannula and having a pointed distal end for piercing tissue and a cavity for receiving tissue to be sampled. In using such a device, the stylet and cannula are relatively positioned so that the distal end of the cannula covers the cavity and closely surrounds the distal end of the stylet to prevent the coring of tissue during insertion into the patient. In one method of using such a device, the stylet and cannula are inserted to a position either in the tissue from which a sample is to be taken or to a point adjacent such tissue. The cannula may then be held stationary with one hand, while the stylet is moved distally with the other hand so that the distal end and the cavity of the stylet move into tissue from which a sample is to be taken. Next, the stylet is held stationary with one hand while the cannula is moved distally thereby cutting tissue that has moved into the cavity. With the tissue sample within the cavity and covered by the cannula, the stylet and cannula are removed from the patient. The body tissue sample may then be removed from the biopsy device for testing purposes.

The above procedure is somewhat complicated and there is the danger of inadvertently moving the wrong member at the wrong time. Because the two members are at times movable together and other times movable relative to each other in performing the biopsy, the person performing the biopsy may inadvertently fail to use the proper sequence of movements or steps in effecting the above procedure. This can, in some cases, result in damage to the patient or failure to obtain a sample thereby requiring a second insertion.

With some biopsy devices it is possible to inadvertently insert the cannula and stylet while the cannula cutting tip is distally of the stylet tip and this would result in damage to body tissue due to coring.

To correct these problems, the invention disclosed in U.S. Pat. No. 4,702,261 to Cornell et al. was invented, the teachings of which are incorporated herein in their entirety as if completely recited herein. In accordance with one aspect of the '261 invention, a biopsy device is provided which includes a cutting member having a cannula which has a distal cutting end, the cannula slidably receiving a stylet having a cavity near the distal end thereof adapted for receiving sample material to be cut by the cannula. The biopsy device includes a housing in which the cannula and stylet members are movable. The '261 device includes means for limiting relative longitudinal movement between the actuators for preventing the distal end of the cutting element from extending distally beyond the distal end of the stylet.

In accordance with another aspect of the '261 invention, a biopsy device is provided which includes a housing, and stylet and cannula members having actuators that are longitudinally slidable relative to each other and the housing, and are disposed in parallel side-by-side relation. An attachable handle may be used.

In accordance with another aspect of the '261 invention, a method of taking a biopsy sample is provided which includes utilizing a biopsy device having a cannula member with a distal cutting end and a stylet member having a cavity and a tissue piercing distal end. The distal ends are inserted into the patient. While holding the housing stationary with one hand, the stylet is advanced to allow tissue to enter the cavity, and then while holding the housing stationary, the cannula is advanced to sever tissue and provide a tissue sample in the stylet cavity.

However, a problem with the prior art biopsy devices is that once a tissue sample has been collected in the stylet cavity, the entire device must be removed from the tissue in order to retrieve the sample. Thereafter, if it is desirable to obtain additional samples, the cannula and stylet must be again inserted into the patient before a sample can be collected. This additional reinsertion of the cannula and stylet very often leads to additional cutting of the patient's tissue. Therefore, it is desirable to create a biopsy device which can take multiple samples without having to reinsert the cannula into the patient for every sample.

SUMMARY OF THE INVENTION

It is therefore an object of the present invention to provide an improved biopsy device wherein one or more of the above problems or disadvantages are overcome.

It is a more specific object to provide a biopsy device which is simpler to use and wherein there is less chance of error in performing the biopsy and therefore less chance of inadvertent damage to the patient.

Still another object is to provide an improved method of obtaining a subcutaneous biopsy.

Briefly, the instant invention comprises a biopsy device having a tubular cannula through which a stylet having a stylet cavity near the distal end is placed. In this regard, the instant invention is very similar to the '261 patented device. However, in the instant invention, the stylet is removable from cannula and removed from the biopsy device through the housing so that the tissue sample obtained by the biopsy device may be retrieved while the cannula of the instant device remains in place within the patient. Thereafter, the stylet may be reinserted through the housing and cannula into the patient's tissue where additional tissue samples may be obtained. In this way, the trauma to the tissue that ordinarily occurs upon reinsertion of the cannula and stylet as in prior art devices has been avoided.

These, as well as other objects and advantages of the present invention, will become more apparent from the following detailed description and accompanying drawings.

BRIEF DESCRIPTION OF THE DRAWINGS

FIG. 3 is a view similar to FIG. 1 but with the biopsy device of FIG. 1 in still another operating condition;

FIG. 4 is a left end view of the device of FIG. 1;

FIG. 5 is a top plan view of the cannula member of the biopsy device of FIG. 1;

FIG. 6 is a right end view of the cannula member of FIGS. 5 and 30;

FIG. 21 is a side elevational view of the biopsy device of FIGS. 1 and 26 on a reduced scale and connected with a handle:

FIG. 22 is a fragmentary right end view of the handle of FIG. 21 with the biopsy device removed;

FIG. 23 is a fragmentary top plan view of the handle of FIG. 21 with the biopsy device removed;

FIG. 26 is a longitudinal cross-sectional view of the second embodiment of a biopsy device in accordance with the present invention;

FIG. 27 is a cross-sectional view similar to FIG. 26 but with the biopsy device in a different operating condition;

FIG. 28 is a view similar to FIG. 26 but with the biopsy device of FIG. 26 in still another operating condition;

FIG. 29 is a left end view of the device of FIG. 26;

FIG. 30 is a top plan view of the cannula member of the biopsy device of FIG. 26;

DETAILED DESCRIPTION OF THE PREFERRED EMBODIMENTS

Figure 1:
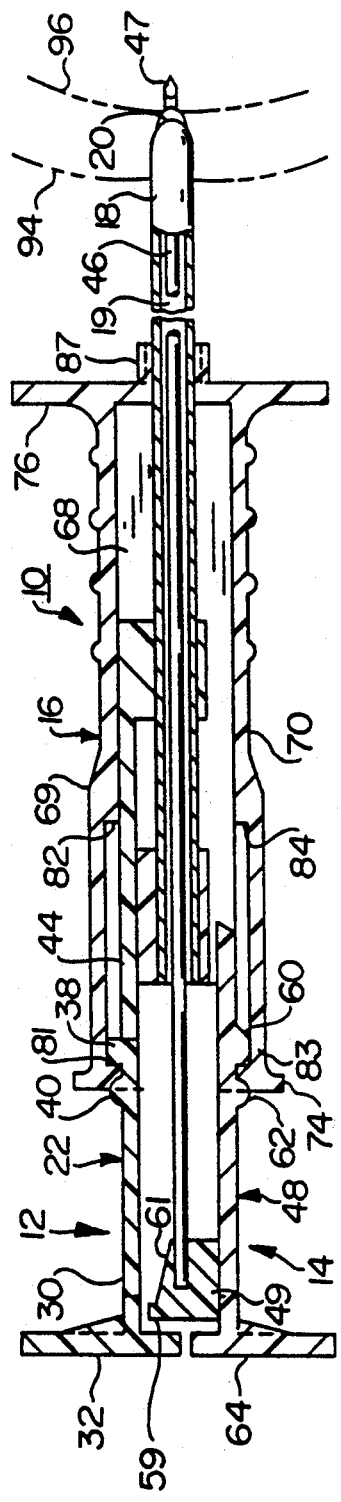
FIG. 1 is a longitudinal cross-sectional view of the first embodiment of a biopsy device in accordance with the present invention.

Two embodiments of the instant invention are disclosed, referred to hereafter generally as the first and second embodiments respectively. Generally speaking, the first embodiment is shown in FIGS. 1–25 while the second embodiment is shown in FIGS. 26–36. Elements common to both embodiments are shown in FIGS. 6, 10–13 and 15–23.

Referring now to the drawings and more particularly to FIGS. 1–4 for the first embodiment and FIGS. 26–29 for the second embodiment, a biopsy device 10 is shown including a tissue cutting member 12, a tissue piercing stylet member 14, and a housing 16 receiving the cutting and stylet members 12 and 14 for predetermined sliding movement relative to each other and to the housing 16. The cutting and stylet members are shown for the two embodiments in three different relative conditions of operation in FIGS. 1, 2, 3, and 26, 27, 28, respectively, which conditions occur during the taking of a biopsy sample. As shown in FIGS. 4 and 29, the proximal end of cutting member 12 is labelled with the word "Cut" to ensure proper identification during use of the biopsy device.

As shown also in FIGS. 5–7 and 30–31, the cutting member 12 includes a tubular cutting element or cannula 18, for example, a stainless steel cylindrical tube having a lumen 19 and a distal cutting end or tip 20. Cutting end 20 is shown pointed and bevel sharpened entirely around the tip for cutting body tissue. The proximal end of cannula 18 is connected to a longitudinally extending actuator 22. Actuator 22 includes a distal end connecting portion 24 which extends normally from the actuator 22 and intersects cannula 18 along the longitudinal axis of cannula 18. In FIGS. 5 and 30, the proximal end of cannula 18 is shown extending through the connecting portion 24 and beyond the proximal side of connecting portion 24 to stylet stop 25. Connecting portion 24 preferably has a reduced width compared to the width of the cannula actuator 22 to facilitate assembling the device 10 and taking multiple biopsy samples so that connecting portion 24 may easily move past rails 85, 86 and safety stops 63, if present, as will be explained hereafter. Cannula 18 may be fixed to portion 24 and stylet stop 25 by an adhesive such as a cured epoxy resin or by other suitable means.

The embodiments of stylet stop 25 corresponding to the two embodiments of the biopsy device are shown in more detail in FIGS. 24-25 and 35-36, respectively. In both embodiments, stylet stop 25 includes a base 27 which is attached to actuator 22 at a location proximal to distal end connecting portion 24. Base 27 is slightly wider than body 31 of stylet stop 25 which extends away from base 27. Both embodiments of body 31 include a bore 37 extending entirely therethrough, which bore 37 encases cannula 18 and provides access to the center of cannula 18 through the proximal end of bore 37 at the proximal end of body 31.

Figure 24:
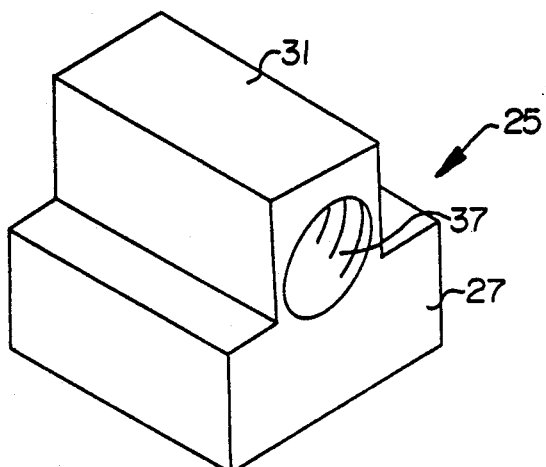
FIG. 24 is a perspective view of the stylet stop of the first embodiment of the instant invention.
Figure 25:
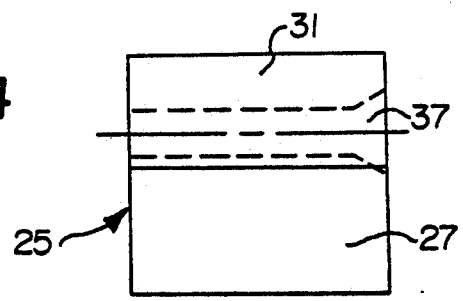
FIG. 25 is a side elevational view of the stylet stop of FIG. 24.
Figure 35:
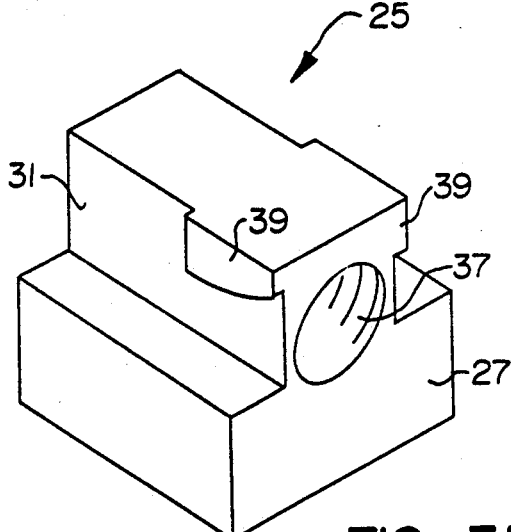
FIG. 35 is a perspective view of the stylet stop of the second embodiment of the instant invention.
Figure 36:
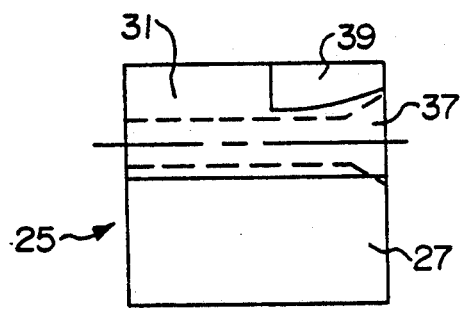
FIG. 36 is a side elevational view of the stylet stop of FIG. 35.
Figure 31:
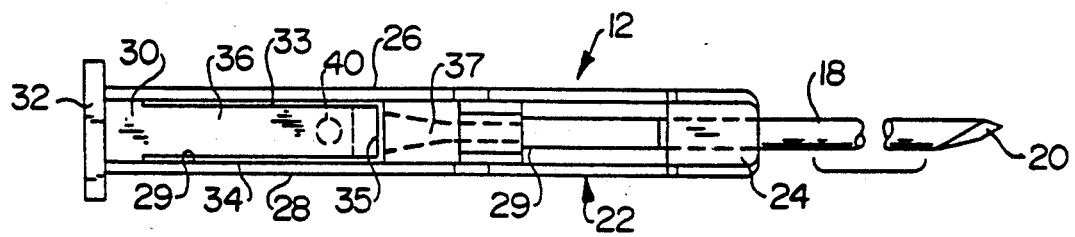
FIG. 31 is a bottom view of the cannula member as shown in FIG. 30.

In the first embodiment shown in FIGS. 24-25, body 31 has smooth sides extending away from base 27. In the second embodiment shown in FIGS. 35-36, a pair of stop lugs 39 are attached to body 31 opposite base 27. Stop lugs 39 extend away from body 31 and provide a channel on each side of body 31 between respective stop lugs 39 and base 27. Stop lugs 39 are tapered with their thickest portions at the more distal end of stop lugs 39 and their more narrow or pointed end at the proximal end of stop lugs 39 for a purpose which will be described hereafter.

Actuator 22 has a pair of opposed upper and lower parallel walls 26 and 28, and an outer sidewall 30 effecting a trough or channel 29. At the proximal end of actuator 22 is a radially outwardly extending flange 32 having a flat proximal side. As shown in FIGS. 4 and 29, corresponding to the first and second embodiments respectively, flange 32 has a notch 32A cut in it for a purpose that will be explained hereafter. A pair of longitudinally extending slots 33 and 34 begin a small distance distal of side wall 30 within channel 29 and extend along channel 29 to a cross slot 35 interconnecting slots 33 and 34 to provide a resilient or spring arm 36. Resilient arm 36 is provided with an abutment 38 at the distal end which serves as a stop and which may be generally rectangular as shown. Spaced a small distance proximally of abutment stop 38 is a radially outwardly extending rounded bump 40.

The stylet member 14, as seen also in FIGS. 8-10 and 32-33, includes an elongate stylet or needle 46 having a pointed sharp distal end 47 for piercing body tissue. The proximal end of stylet 46 is connected to a stylet actuator 48 at the proximal end of actuator 48 through proximal end portion 49. Stylet 46 is preferably fixed to proximal end portion 49 by a cured epoxy resin but may be attached by other suitable means.

Figure 9:
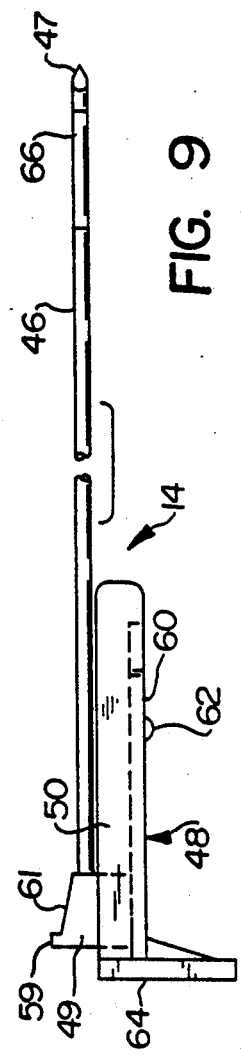
FIG. 9 is a top plan view of the stylet member of FIG. 1.
Figure 10:
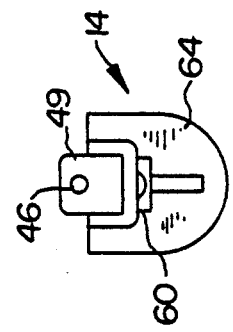
FIG. 10 is a right end view of the stylet member of FIGS. 9 and 33.
Figure 11:
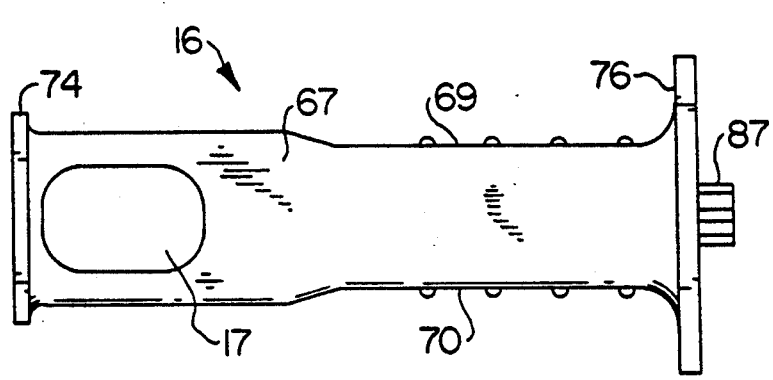
FIG. 11 is a top plan view of the housing of FIGS. 1 and 26.
Figure 33:
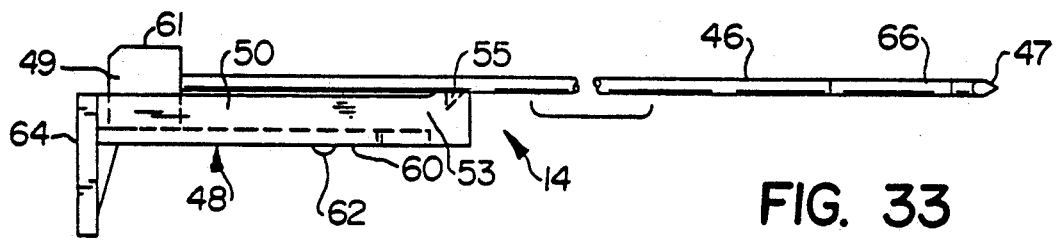
FIG. 33 is a top plan view of the stylet member of FIG. 26.
Figure 34:
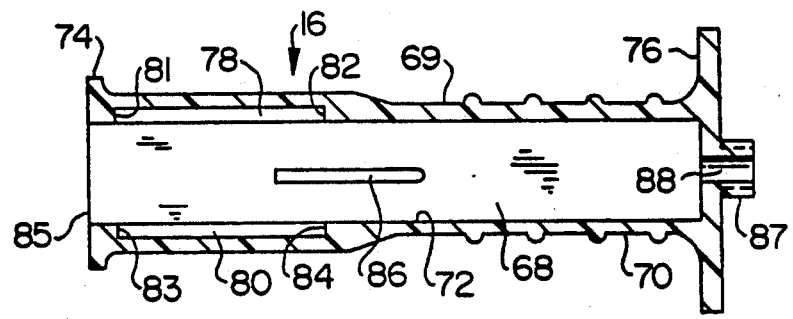
FIG. 34 is a longitudinal cross-sectional view of the housing of the second embodiment of the instant invention.
Figure 37:
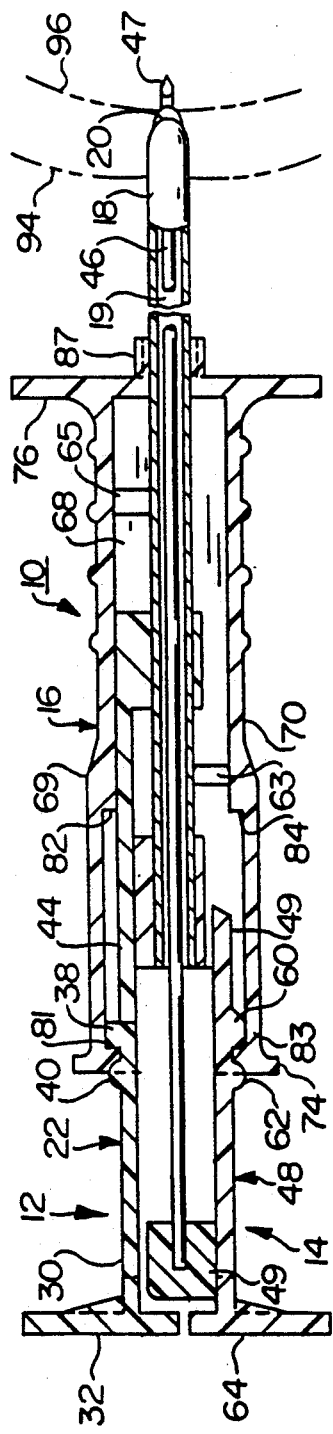
FIG. 37 is a longitudinal cross-sectional view of an alternate embodiment of the invention incorporated into the second embodiment of the biopsy device in accordance with the present invention.

In the first embodiment, as shown in FIG. 9, the proximal end portion 49 has a extended protrusion or tip 59 at the proximal end thereof. A sloping upper surface 61 extends from the tip 59 toward stylet 46. Tip 59 contacts side wall 30 to restrain proximal movement of stylet actuator 48 relative to cannula actuator 22 as will be explained hereafter. In the second embodiment, as shown in FIG. 33, the proximal end portion 49 has no protrusion corresponding to tip 59, but instead maintains a comparatively low profile with an upper surface 61 being generally parallel to and slightly above stylet 46.

Actuator 48 includes upper and lower parallel walls 50 and 51, respectively, and an outer sidewall 52 connecting the upper and lower walls so as to form a channel. Wall 52 includes a pair of longitudinally extending slots 54 and 56 and a distal end cross slot 57 connecting slots 54 and 56 to form a resilient spring-like member 58.

Figure 32:
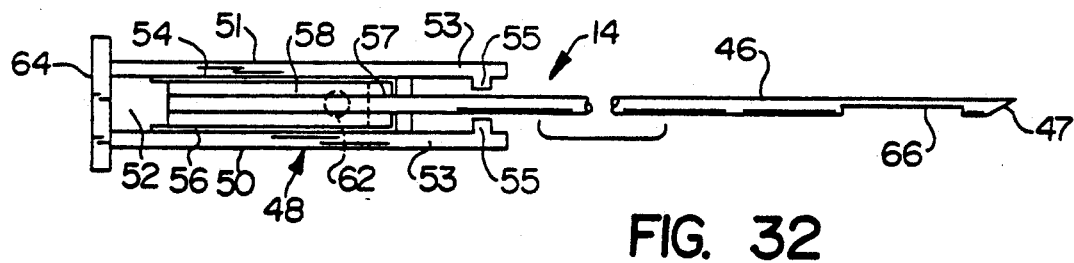
FIG. 32 is an upper side view of the stylet member of the biopsy device of FIG. 26.

The resilient member 58 has an integral, substantially rectangular abutment or stop 60 and a bump 62 spaced slightly proximally of the abutment 60. Stop 60 is preferably beveled at an angle of about 45° at its most distal end. This beveled angle facilitates reinsertion of the stylet actuator 48 into the housing 16 as will be explained hereafter. A pair of stylet actuator extenders 53 extend from the proximal end of upper and lower parallel walls 50 and 51, along the side of stylet 46. Stylet actuator extenders 53 are spaced apart to allow body 31 to pass therebetween in the first embodiment and to allow body 31 and a pair of locking lugs 55 to pass therebetween in the second embodiment. In the second embodiment as shown in FIGS. 32 and 33, each stylet actuator extender 53 has a locking lug 55 located on its distal end and directed towards the locking lug 55 on the other stylet actuator extender 53 so that the locking lugs 55 on each of the stylet actuator extenders 53 are opposed. As best seen in FIG. 33, locking lugs 55 are tapered from their narrowest part at their distal end to their widest part at their proximal end to form a wedge shape. Locking lugs 55 are located on stylet actuator extender 53 in a position closest to stylet 46. Locking lugs 55 contact stop lugs 39 on stylet stop 25 to limit relative longitudinal movement between the cutting member 12 and stylet member 14 as will be discussed hereafter.

Actuator 48 also has a flange 64 extending in the opposite direction from that of flange 32 of cutting member 12 as viewed in FIGS. 1-3 and 26-28. Flange 64 also has a flat proximal side. The stylet 46 has a longitudinally extending groove or cavity 66 in the sidewall of the needle which is adapted to receive body tissue to be sampled. Stylet 46 is solid and circular in cross-section and is sized to be slidably received in the lumen 19 of cannula 18 as shown in FIGS. 1-3 and 26-28. Stylet 46 is preferably made of stainless steel.

Figure 12:
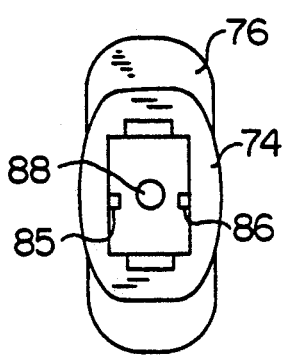
FIG. 12 is a left end view of the housing of FIG. 11.
Figure 13:
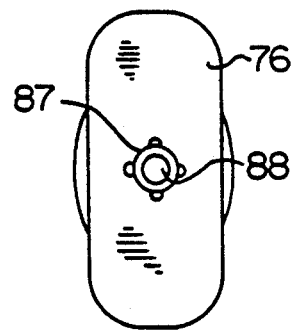
FIG. 13 is a right-hand end view of the housing of FIG. 11.
Figure 14:
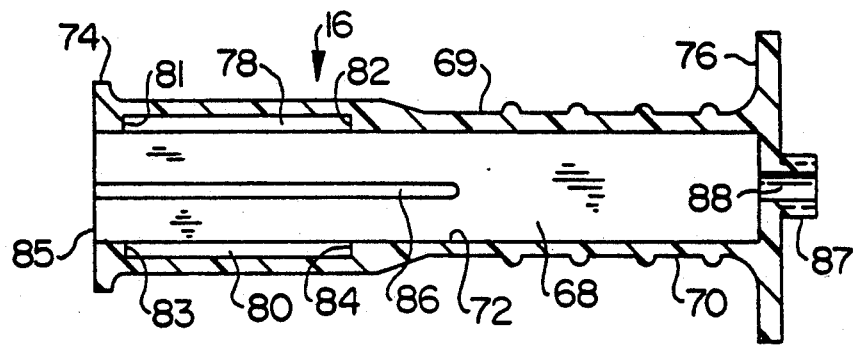
FIG. 14 is a longitudinal cross-sectional view of the housing of the first embodiment of the instant invention.
Figure 18:
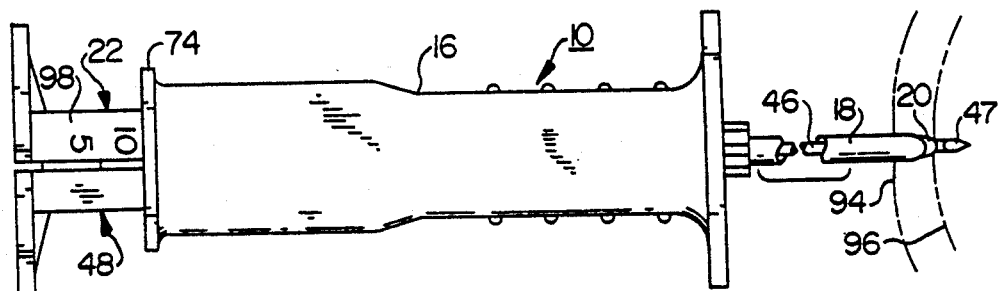
FIG. 18 is a top plan view of the biopsy device of FIGS. 1 and 26 but with the housing positioned for taking a tissue sample of smaller length.

Housing 16, as also seen in FIGS. 11-14, has longitudinally extending upper and lower sides 67 and 68, and opposed sidewalls 69 and 70 providing a longitudinally extending chamber 72 for receiving the tissue cutting and stylet members 12 and 14. The housing 16 is generally rectangular in cross-section and completely encircles or surrounds the cutting and stylet members 12 and 14. The housing 16 has a flange 74 at its proximal end and a flange 76 at its distal end which extend entirely around the housing 16 as best seen in FIGS. 12 and 13. Sidewalls 69 and 70 have a pair of grooves 78 and 80, respectively, which extend distally from flange 74. Groove 78 has proximal and distal end walls 81 and 82 which form stops engageable with stop 38 on the cutting member 12 to limit movement of the cutting member in both distal and proximal directions of movement. The groove 80 in wall 70 has proximal and distal end walls 83 and 84 which serve as stops for abutment stop 60 on stylet 14 to limit similar movement thereof. However, because of the beveled surface of abutment stop 60 as explained above, the contact between the beveled surface of abutment stop 60 and distal end wall 84 may not provide a secure stop to keep stylet actuator 48 from moving into the area distal of distal end wall 84. Therefore, a pair of safety stops 63 are provided attached to the insides of upper and lower sides 67, 68 respectively to contact the distal end of the stylet actuator extender 53 closest to the respective upper and lower sides 67, 68 when abutment stop 60 is in contact with distal end wall 84. Safety stops 63 extend inward from their respective upper and lower sides 67, 68 a sufficient distance to contact and prevent stylet actuator extenders 53 from moving further distally, but they do not extend so far from their respective upper and lower sides 67, 68 to contact the connecting portion 24 or the body 31 of stylet stop 25 should cutting member 12 be moved to bring connecting portion 24 or stylet stop 25 near safety stops 63.

On the inner sides of the upper and lower walls 67 and 68 of the housing 16 are a pair of rails 85 and 86, respectively, on which the actuators 22 and 48, respectively, slide when the cutting and stylet members 12 and 14 are moved in the housing. In the first embodiment shown in FIG. 14, rails 85,86 extend from the proximal end of housing 16 to a position approximately midway between flange 74 and flange 76. In the second embodiment, as can best be seen in FIG. 34, rails 85 and 86 do not extend to the proximal end of housing 16. Instead, they terminate some distance from the proximal end to allow stylet member 14 to move toward cutting member 12 when cutting member is in its most proximal positions to remove stylet 46 from the biopsy device as will be described hereafter.

Housing 16 is also provided with a collar 87 at the distal end thereof which has a passage 88 connected with the chamber 72 to closely receive the cannula 18 in sliding relation. Housing 16 also preferably includes at least one window 17 located in upper or lower side 66, 67 or both. If such a window 17 is present, rails 85 and 86 must necessarily terminate prior to reaching window 17. In the case of the first embodiment, the part of rails 85,86 extending distally of window 17 is sufficient to allow actuators 22 and 48 to slide within housing 16. Window 17 allows the operator of the device 10 see the bore 37 on stylet stop 25 when removing and inserting stylet 46 as will be explained hereafter.

Figures 15, 16:
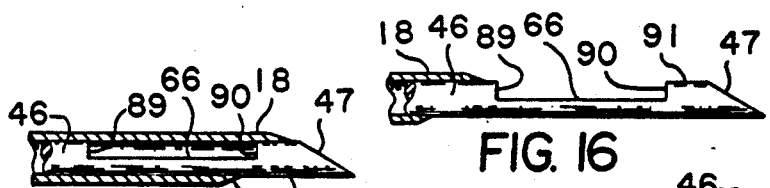
FIG. 15 is an enlarged fragmentary view of the distal end portions of the stylet and cannula of FIGS. 1 and 26 rotated 90°.
FIG. 16 is an enlarged fragmentary view of the distal end portions of the stylet and cannula of FIGS. 1 and 26 rotated 90°.
Figure 17:
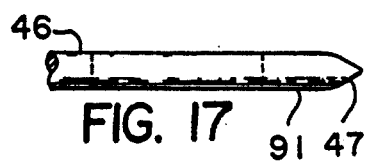
FIG. 17 is an enlarged bottom view of the distal end portion of the stylet of FIGS. 1 and 26.

As best seen in FIGS. 15 and 16, the cavity 66 of the stylet 18 is spaced from but near the distal end or tip 47 of the stylet. The cavity 66 has opposed proximal and distal end walls 89 and 90 and may be formed by grinding or the like. When the cannula 18 is in its distal or forwardmost position with respect to the stylet 46, as in FIGS. 1 or 26 and FIG. 15, the cannula completely covers the cavity 66 with the tip 20 of the cannula on a cylindrical distal end portion 91 of the cannula. With the cannula 18 and stylet 46 relatively positioned as in FIGS. 1 or 26, they can be inserted into a desired location in the body tissue without coring tissue during the insertion. FIG. 16 shows the cannula 18 retracted or in its most proximal or rearward position with respect to the stylet 46 so that the cavity 66 is fully uncovered and the cannula surrounds a cylindrical portion of the stylet which is proximal of the cavity. The outer surface of the bottom wall of the cavity 66 is arcuate or rounded as shown in FIG. 17.

When assembling the biopsy device 10, the distal tip 47 of stylet 46 is inserted into the proximal end of lumen 19 of cannula 18 through bore 37 in stylet stop 25. As stylet 46 is pushed through cannula 18, end portion 49 of the stylet actuator 48 approaches flange 32. In both embodiments, notch 32A allows stylet 46 to pass through flange 32 into housing 16 and subsequently into bore 37 of stylet stop 25. In the first embodiment, tip 59 must be slightly moved away from flange 32 in order to allow end portion 49 to enter channel 29. In the second embodiment, end portion 49 passes through notch 32A and enters the channel 29 of the cannula actuator 22.

In the first embodiment, stylet actuator 48 is free to move distally, thereby moving stylet 46 in cannula 18, until stylet actuator extenders 53 contact safety stops 63. In the second embodiment, as stylet actuator 48 is pushed toward the distal end of cannula actuator 22, locking lugs 55 will contact stop lugs 39. Because of the tapering of both locking lugs 55 and stop lugs 39, as locking lugs 55 contact stop lugs 39, locking lugs 55 will be driven up over locking lugs 39 toward the body of cannula actuator 22 until passing by stop lugs 39. Thereafter, as stylet actuator 48 is moved further distally, then due to the resiliency of stylet actuator extenders 53, locking lugs 55 will cease their contact with locking lugs 39 and move away from the body of cannula actuator 22 into the area between stylet stop 25 and distal end connecting portion 24. Locking lugs 55 will move freely in the area between stylet stop 25 and distal end connecting portion 24 along an axis parallel to cannula 18. Before the assembled cannula actuator 22 and stylet actuator 48 are placed in housing 16 as will be explained hereafter, stylet actuator 48 is constrained in its distal motion by contact between proximal end portion 49 and stylet stop 25.

After locking lugs 55 have moved into the area between stylet stop 25 and distal end connecting portion 24, stylet actuator 48 is constrained in proximal motion by the contact between the wider portion of locking lugs 55 and the wider portion of tapered stop lugs 39. Both locking lugs 55 and stop lugs 39 are located on their respective stylet actuator extenders 53 and body 31 so that flange 32 and flange 64 will be aligned when locking lugs 55 and stop lugs 39 abut each other to constrain the more proximal movement of stylet actuator 48 relative to cannula actuator 22.

With stylet 46 within the cannula 18, stylet 46 and cannula 18 are inserted into the proximal end of housing 16 and through the distal opening 88 (FIGS. 14 and 34) with the actuators entering the housing and with the housing rails 85 and 86 between the actuators. Next, the resilient spring members 36 and 58 may be pinched toward each other to move the abutments 38 and 60 inwardly past the housing end abutments 81 and 83. In this regard, the beveled distal end of abutment 60, if present, allows abutment 60 to more easily pass housing end abutment 83. When released, the cannula and actuator members 12 and 14 are slidably disposed in housing 16.

In the assembled biopsy device 10, the cannula and stylet members 12 and 14 are limited in movement in the proximal direction by the engagement of the actuator stops 38 and 60 with the housing stops 81 and 83, respectively, as in FIGS. 1 and 26. In FIGS. 1 and 26, the members 12 and 14 are in the fully retracted or maximum proximal or rearward position.

The movement of the cannula and stylet member 12 and 14 in the distal direction is limited by the engagement of the actuator stops 38 and 60 with the housing stops 82 and 84, respectively and by contact between the distal end of stylet actuator extenders 53 and safety stops 63, if present. Members 12 and 14 are shown in FIGS. 3 and 28 in the maximum distal or extended position.

In the first embodiment, the tip 59 contacts flange 32 to limit proximal movement of the stylet actuator 22 relative to cannula actuator 48 to positively prevent the cannula tip 20 from moving distally of the distal tip 47 of stylet 46. In this embodiment, interaction between tip 59 and side wall 30 ensures that the operator of device 10 cannot, under any circumstance, insert the device 10 into the body tissue with the cannula tip extending distally of the stylet tip, thereby causing coring.

In the second embodiment, locking lugs 55 (FIG. 32) cooperate with stop lugs 39 to limit proximal movement of the stylet actuator 22 relative to the cannula actuator 48 to positively prevent the cannula tip 20 from moving distally of the distal tip 47 of the stylet 46. This ensures, in this embodiment, that the operator of device 10 cannot, under any circumstance, insert the device 10 into body tissue with the cannula tip extending distally of the stylet tip, thereby causing coring.

Whenever the actuators are positioned such that the actuator flanges 32 and 64 are substantially equidistant from the flange 74 of housing 16, that is flanges 32 and 64 are aligned in the same plane as shown in FIGS. 1, 3, 26, and 28, the cannula 18 covers the cavity 66 of the stylet as best seen in FIG. 15. Thus, the operator of the device 10 will readily know when the device can be inserted into a patient without the cavity 66 being exposed.

In operation, preparatory to insertion of the device 10 into the tissue of a patient, indicated at 94, the cannula and stylet members 12 and 14 are retracted or moved to their most proximal positions as shown in FIGS. 1 and 26. In this condition, the friction bumps 40 and 62 of the actuators engage the proximal end of housing flange 74 to resist inadvertent distal movement of the actuators relative to the housing. In this condition, the cavity 66 is covered by the cannula 18. Since spring arm 36 and spring member 68 are slightly flexible, such resistive forces due to the bumps 40 and 62 are overcome when manual forces are applied to the members to urge them into the housing 16.

Figure 2:
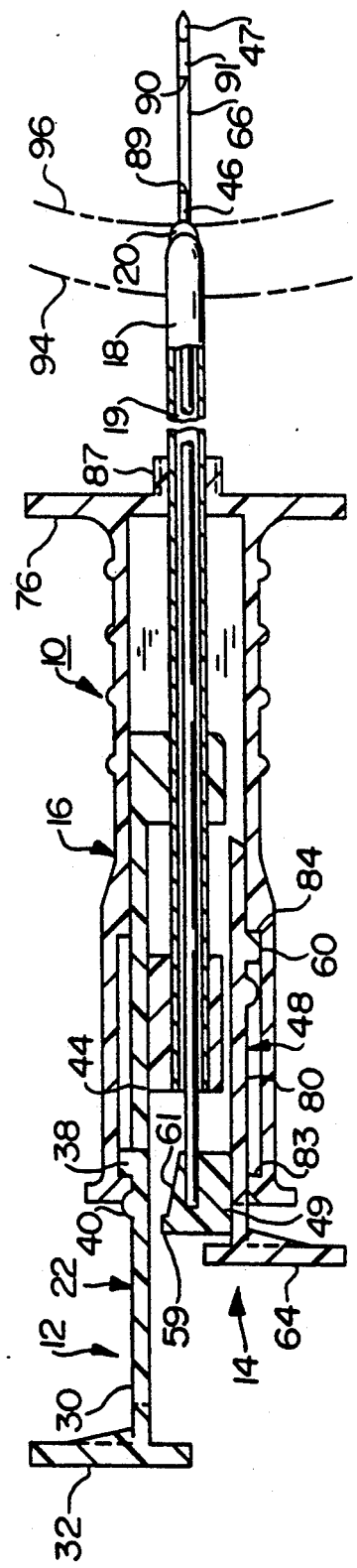
FIG. 2 is a cross-sectional view similar to FIG. 1 but with the biopsy device in a different operating condition.
Figure 7:
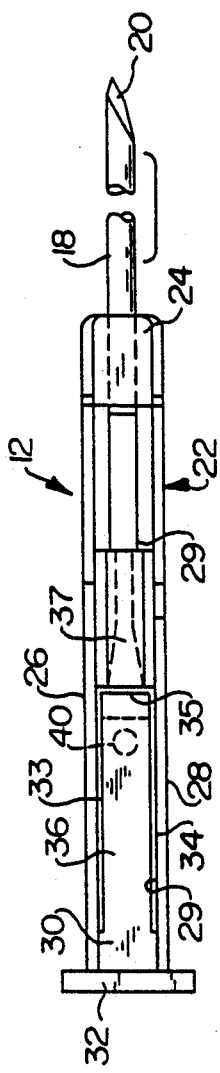
FIG. 7 is a bottom view of the cannula member as shown in FIG. 5.
Figure 8:
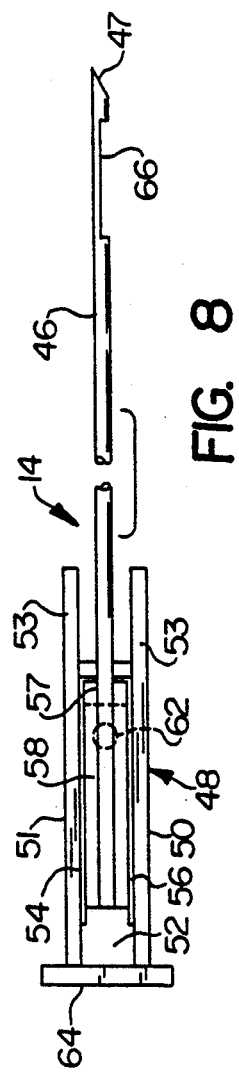
FIG. 8 is an upper side view of the stylet member of the biopsy device of FIG. 1.

With the members 12 and 14 positioned as shown in FIGS. 1 and 26, the housing 16 may be grasped by the hand to move the distal tips 20 and 47 of the members 12 and 14 into the patient and up to that area of the body 96 from which a sample is to be taken. When the biopsy device 10 is properly positioned in the patient, the housing 16 may be held stationary with one hand while the stylet actuator 48 is moved distally to its full distal position as shown in FIGS. 2 and 27 wherein the stop 60 engages housing stop 84 at the distal end of housing groove 80. During this movement, the cannula 18 and housing 16 remain stationary while the stylet 46 is moved distally relative to the cannula 18 and into the tissue material 96 from which a sample is to be taken. The engagement between the bump 40 and proximal end of housing 16 prevents any inadvertent movement of the cannula actuator 22 at this time. In the position shown in FIGS. 2 and 27, tissue material 96 from which a sample is to be taken will extend into the cavity 66 and the condition of the cannula 18 and stylet 46 will appear as in FIG. 16, that is, with cavity 66 fully open.

Next, while still holding the housing 16 stationary in the same hand, the cannula actuator 22 is moved distally from its position in FIGS. 2 and 26 to its full distal position as shown in FIGS. 3 and 28, respectively. In its full distal position, the cannula actuator stop 38 engages stop 82 at the distal end of the housing groove 78. During this movement, the cutting end 20 of the cannula 18 cuts sample material 96 that extends into the cavity 66 and returns the cannula 18 and stylet 46 to the positions indicated in FIG. 15 but with the cavity 66 containing the severed tissue sample (not shown). The biopsy device 10 may then be removed from the tissue 94 of the patient with the sample being maintained in the cavity 66 by the cannula 18. The cannula 18 may then be retracted or moved proximally relative to the stylet 46 to open the cavity 66 and permit removal of the tissue sample for test purposes.

However, if multiple samples of tissue from the sample area 96 are to be taken, instead of removing the entire biopsy device 10 before the respective samples may be collected, cannula 18 of the biopsy device 10 may remain in the patient's tissue 94 and the stylet 46 with the cavity 66 containing the sample removed from the biopsy device 10. This is accomplished by retracting or moving cannula actuator 22 and stylet actuator 48 to their most proximal position so that bumps 40 and 62, respectively, are positioned proximally to flange 74 of housing 16. Thereafter, while holding housing 16 with one hand, the operator may depress bump 62 with the finger or fingernail of one hand thereby pushing spring arm 58 toward cannula actuator 22.

In the first embodiment, as spring arm 58 is pushed towards cannula actuator 22, the operator simultaneously lifts the proximal end of stylet actuator 48 so that the tip 59 of proximal end portion 49 is moved above side wall 30. Thereafter, as the user moves stylet actuator 48 proximally, end portion 49 will move over side wall 30 thereby allowing stylet 46 to move out of cannula 18 and out of housing 16. Thereafter, the sample may be removed from recess 66.

In the second embodiment, as spring arm 58 is pushed towards cannula actuator 22, locking lugs 55 are pressed toward cannula actuator 22 below stop lugs 39 on stylet stop 25. In this configuration, slight proximal pressure on flange 64 moves locking lugs 55 proximal of stop lugs 39 while simultaneously passing stop 60 beyond flange 74. Thereafter, stylet actuator 48 may be moved proximally until the distal end 47 of stylet 46 moves clear of bore 37 and stylet stop 25. At this time, stylet 46 is free to be removed from housing 16 and cavity 66 is exposed so that the sample collected may be removed from cavity 66.

In both the first and second embodiments, to reinsert stylet 46 into cannula 18 for repeated taking of samples, the distal end 47 of stylet 46 is positioned at bore 37, and stylet 46 aligned with cannula 18 so that stylet 46 may be moved distally through cannula 18. In this regard, window 17 allows the operator to see the proximal end of bore 37 to aid in aligning the distal end 47 of stylet 46 with the proximal end of bore 36. As the proximal end portion 49 approaches the flange 32 in embodiment one, the small notch 32A in flange 32 allows stylet 46 to pass into cannula 18.

In the first embodiment, when the proximal end portion 49 with tip 59 approaches flange 32, stylet actuator 48 is flexed slightly away cannula actuator 22 so that tip 59 may move over flange 32 and into channel 29. As stylet actuator 48 moves into housing 16, bump 62 may be depressed so that stops 60 may move past flange 74 into groove 78 which constrains stylet actuator 48 in movement within housing 16 as explained above. The beveled distal surface of stop 60 allows stop 60 to more easily pass flange 74.

In the second embodiment, stylet actuator 48 is aligned so that proximal end portion 49 may pass through notch 32A. Thereafter, stop 60 comes into contact with the proximal side of flange 74. To move stylet actuator 48 into its operative position, stop 60 is depressed by the finger of the operator while pressure is put on flange 64 in the distal direction to move stop 60 past flange 74 and consequently needle actuator 48 further into housing 16 until bump 62 comes into contact with the proximal surface of flange 74. Once again, the beveled distal surface of stop 60 facilitates the movement of stop 60 past flange 74. In this position, biopsy device 10 has cavity 66 contained within cannula 18 and is ready for taking another sample.

The procedure for taking samples in both embodiments is identical to that described above. In this way, multiple samples may be taken without having to remove the entire biopsy device. Further, multiple samples can be taken within the same initial puncture wound so that the distal end 47 of stylet 46 in the distal cutting end of cannula 18 do not have to re-travel the length of the initial puncture wound for every sample. If additional samples are required in the same general area, pressure may be placed on the biopsy device 10 to move slightly to one side or the other or the biopsy device 10 may be moved further along the puncture wound to take samples from sights deeper within the tissue 96.

Because of the use of housing 16, the operation of the device 10 is simple and the risk of operating errors and inadvertent damage to the patient is reduced. Since housing 16 may be held stationary with one hand after the insertion of the device 10 into the patient, the housing provides a stable reference point with respect to the patient and for the subsequent movements of the cannula and stylet members 12 and 14 in properly obtaining the desired tissue sample. This method and operation of device 10 is simple in that after initial insertion of the device 10 while in the condition shown in FIGS. 1 and 26, both actuators 22 and 48 are manually pushed forward, first the stylet actuator 48 and then the cannula actuator 22.

The biopsy device 10 may be operated in a somewhat different manner from that previously described herein. For example, the actuators 22 and 48 may be initially moved fully forward or to their most distal positions as shown in FIGS. 3 and 28 and, while holding the actuators in these positions, inserting the cannula 18 and stylet 46 fully into the tissue 96 to be biopsied such as shown in FIGS. 3 and 28. Then, while maintaining the housing 16 and stylet 48 stationary, the cannula actuator 22 is moved proximally to its most proximal position such as to the position shown in FIGS. 2 and 27. By moving the cannula in the proximal direction, the cavity 66 is exposed to allow tissue 96 to enter the cavity 66. The next step is to move the cannula actuator 22 forward or distally while maintaining the stylet 46 and housing 16 stationary to thereby cut body tissue 96 and trap it in the cavity 66 of the stylet 46. While so trapped, the biopsy device 10 may then be removed from the patient or only the stylet 46 removed from the biopsy device 10 to retrieve the sample as described above. This method is also simple since only cannula actuator 22 is moved after the device 10 is inserted, that is, actuator 22 is first moved proximally to open the stylet cavity 66 and then it is moved distally to effect the cutting of the tissue.

In both of the above described procedures, the housing 16, after the device 10 is initially inserted into the patient, remains stationary to limit the movements of the actuators in obtaining the desired biopsy specimen and to provide a stable reference point for indicating the relative positions of the cannula 18 and stylet 46 when in the patient.

The biopsy device 10 may also be used to remove a biopsy specimen of smaller length than that obtained by the above two procedures. For example, with the biopsy device 10 in the condition shown in FIGS. 1 and 26, that is, with the cannula and stylet members 12 and 14 in the fully retracted or most proximal positions, the device 10 is inserted into the patient to a point adjacent the tissue 96 from which a sample is to be taken. After insertion and while holding the actuators 22 and 48 stationary, the housing 16 is moved a selected amount proximally relative to the actuators. A scale 98 (FIGS. 5, 18, 19, and 30) is provided on the cannula actuator 22 to indicate the amount of movement of the housing from its position in FIGS. 1 and 26 to its position in FIG. 18. For example, the scale may be in millimeters.

Figure 19:
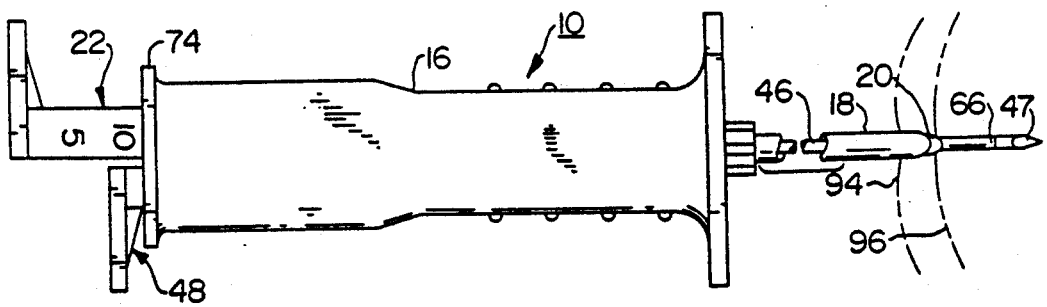
FIG. 19 is a plan view similar to FIG. 18 but with the stylet and cannula members in a different operating condition.
Figure 20:
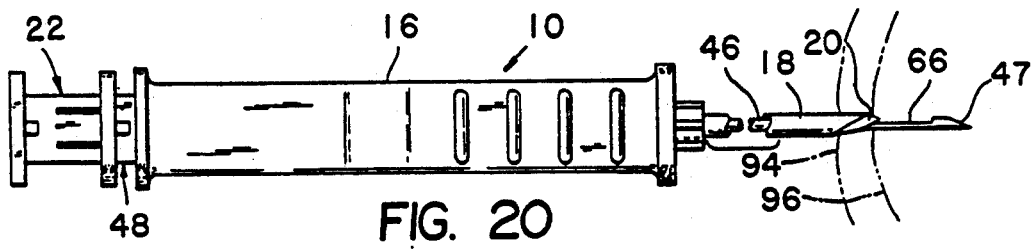
FIG. 20 is a bottom view of the biopsy device as shown in FIG. 19.
Figure 38:
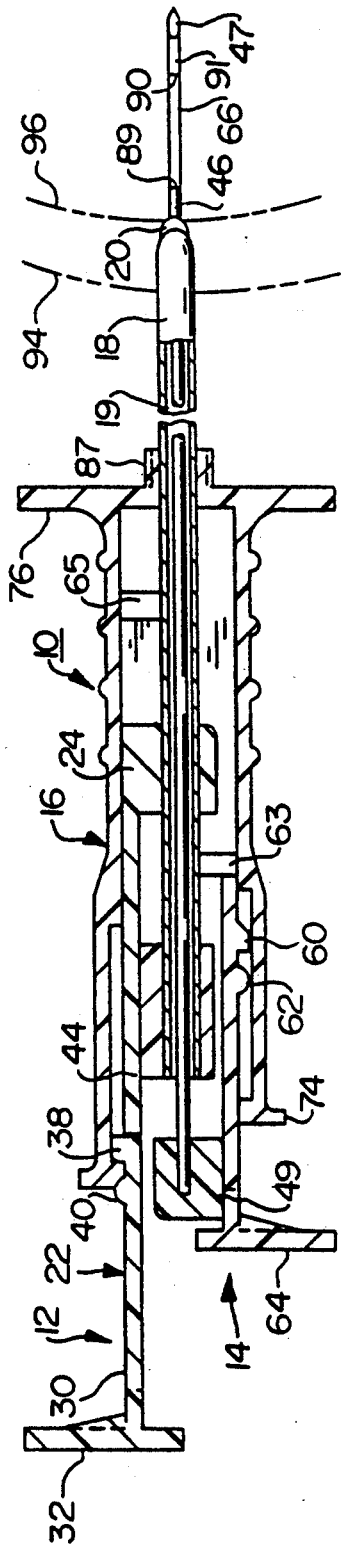
FIG. 38 is a cross-sectional view similar to FIG. 37 but with the biopsy device in a different operating condition.

Next, while maintaining the housing 16 and cannula actuator 22 stationary, the stylet actuator 48 is moved proximally into housing 16 as far as it will go, such as shown in FIG. 19. The distal advancement of the stylet actuator 22 is stopped as a result of the engagement between the housing stop 84 and stylet actuator stop 60. Since the housing 16 had been moved proximally, the advancement of the stylet actuator 22 relative to the cannula actuator 22 is reduced. This means that the length of the cavity uncovered by the cannula 18 (FIG. 19) is less than the full length of the cavity and is represented by the position of the housing flange 74 on the scale 98. With the device 10 in the condition shown in FIGS. 19 and 20, the cannula actuator 22 is moved distally until it is stopped by the engagement between stop 38 on cannula actuator 22 and stop 82 on housing 16. This latter movement of the cannula cuts the body tissue and closes cavity 66 so that the device 10 may be removed from the patient along with the sample. In this case, the length of the sample will be less than that obtained when the full length of the cavity 66 is used to receive sample tissue.

Where the biopsy device 10 has a small diameter cannula 18, as for example an 18 gauge cannula, the corresponding stylet 46 will also have a small diameter. In this case, it is often desirable to reduce the size of cavity 66 in stylet 46 to reduce the possibility that during the biopsy procedure, the stylet 46 will bend at cavity 66 due to the reduced thickness of stylet 46 at cavity 66. When a cavity 66 of reduced size is used, it is desirable to limit the movement of the cannula actuator 22 and the stylet actuator 48 in the proximal and distal direction so that only the cavity 66, and not the stylet 46 proximal to cavity 66, is exposed by proximal movement of stylet actuator 48 relative to cannula actuator 18. This is accomplished as shown in FIGS. 37-41 by placing safety stops 63 along upper and lower sides 67, 68 (FIGS. 40 and 41) so that when cannula actuator 18 is in its most proximal position, the stylet actuator 48 may be moved to its most distal position where stylet actuator extenders 53 contact safety stops 63 (FIG. 38). In this configuration, only the cavity 66 and not the stylet 46 proximal to cavity 66 will be exposed.

Figure 39:
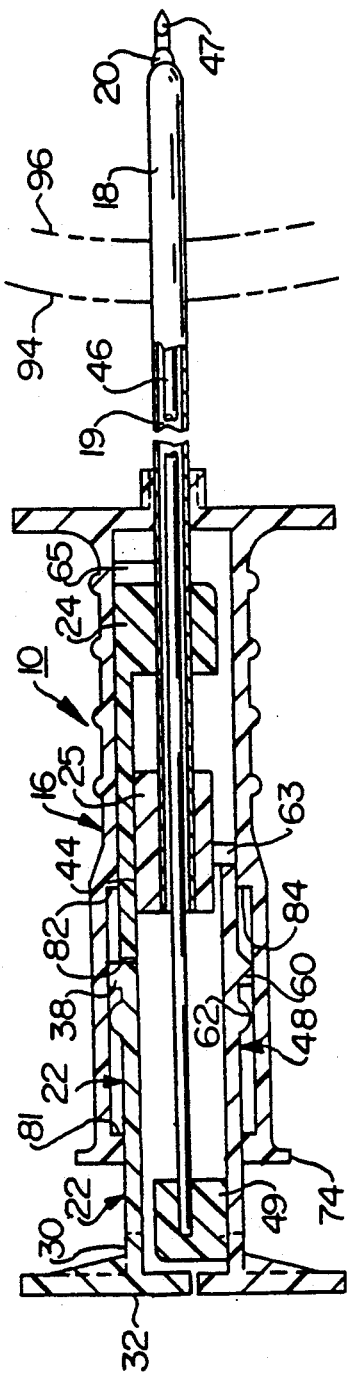
FIG. 39 is a view similar to FIG. 37 but with the biopsy device of FIG. 37 in still another operating condition.
Figure 40:
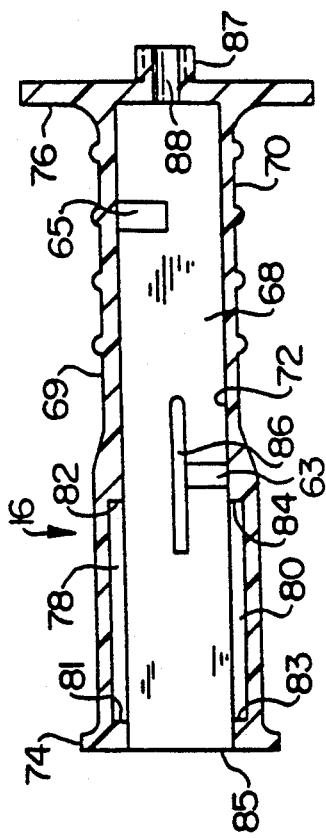
FIG. 40 is a longitudinal cross-sectional view of the housing of the first embodiment modified according to the alternate embodiment of the invention shown in FIGS. 37 through 39.
Figure 41:
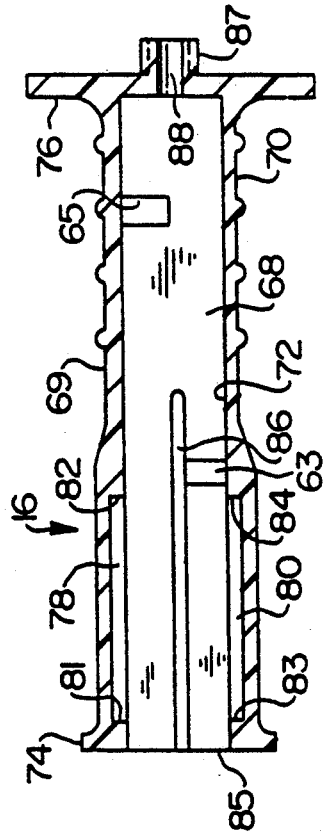
FIG. 41 is a longitudinal cross-sectional view of the housing of the alternate embodiment of the second embodiment of the instant invention shown in FIGS. 37 through 39.

In order to prevent cannula 18 from moving distally beyond the distal end 47 of stylet 46, a cannula stop 65 is located on upper and lower sides 67, 68 (FIGS. 40 and 41) to contact connecting portion 24 and prevent it from moving distally of cannula stop 65 (FIG. 39). Cannula stop 65 should be positioned on upper and lower sides 67, 68 so that when connecting portion 24 contacts cannula stop 65 and stylet actuator extenders 53 contact safety stop 63, flanges 32 and 64 will be aligned (FIG. 39).

FIGS. 21-23 illustrate an embodiment in which the biopsy device 10 is connected to a hand grip 100 so that the device 10 may be readily used with one hand thereby freeing the other hand for other work. Hand grip 100 includes an elongate platform 102 which supports the housing 16. The platform extends between the housing flanges 74 and 76 to provide a tight fit therebetween. The platform 102 includes a flat bottom supporting wall 104, a pair of opposed sidewalls 106 and 108 which respectively engage the opposed sides 69 and 70 of the housing. These sidewalls 106 and 108 are curved as seen in FIGS. 22 and 23 so as to extend slightly over the upper wall 67 of the housing to firmly hold the housing in place on the platform. At the distal end of platform 102 are a pair of integral upstanding walls 110 and 112 that engage the proximal side of the housing flange 76. Connected to the platform is a depending handle 114 adapted to be gripped by the hand. In this way, the handle 114 may be gripped by the hand and the thumb used to operate the actuators 22 and 48 from the proximal end of the device 10. The handle 114 has a flat, relatively thin web 116 with a wider peripheral border 118. The border widens near platform 102 to form a thumb rest area indicated at 120. The plane of the web 116 is closer to the plane of sidewall 106 than to the plane of sidewall 108 to allow a more natural and comfortable positioning of the thumb.

The hand grip 100 is preferably a single piece molded plastic member of relatively rigid plastic. The plastic should be flexible enough to allow the housing 16 to be manually inserted onto the platform 104 when forced between the sidewalls 106 and 108. These sidewalls should be resilient enough to firmly grip the housing during use. The handle 100 and device 10 may be assembled by first forcing the narrow distal portion of housing 16 between the resilient walls 106 and 108 of the handle. Then the housing 16 may be moved distally until the housing flange 76 passes the distal end of the platform 102. The sidewalls then resiliently engage the enlarged proximal portion of the housing.

The device 10 may be removed from the handle 100 by holding housing flange 76 stationary with one hand and gripping handle 100 by the other hand. Then, forcing the distal end of platform 102 downwardly and angularly away from the housing 16, that is, tilting the distal end of the platform 102 downwardly and away from the distal end of the housing. As the platform moves angularly away from the housing, the wider portion of the housing is forced through the resilient sidewalls 106 and 108 of the handle to free the device 10. The handle 100 may be repeatedly used with biopsy devices either identical to device 10 or other similarly dimensioned medical devices.

The actuators 22 and 48, the housing 16, and the hand grip 100 may be formed or molded of a relatively rigid plastic such as an acrylonitrile butadiene styrene (ABS), a polycarbonate, a polysulfone, a polyphenylene oxide or other similar plastic. Preferably, the hand grip 100 is not made of (ABS) because ABS is not sterilizable by autoclaving. The use of autoclavable material for hand grip 100 allows the hand grip 100 to be sterilized by autoclaving so that the hand grip 100 may be reused up to about 100 times. Although the preferred embodiment of hand grip 100 is autoclavable and therefore reusable, the biopsy device 10 is preferably not reusable so that a new device 10 is used for each biopsy session. After each biopsy session, the biopsy device 10 is disposed of.

When operating the device 10 with the handle 100 attached, the steps and movements of the parts may be the same as those previously described herein except that the thumb can be used to operate the actuators.

The housing 16 as constructed and shown is symmetrical so that the actuators 22 and 48 can be assembled with housing 16 even when the housing is rotated 180° on its longitudinal axis from the orientation shown in the drawings.

As various changes could be made in the above described construction and method without departing from the true spirit and scope of the invention, it is intended that all matter contained in the above description and shown in the accompanying drawings be interpreted as illustrative.

We claim:

1. A biopsy device for sampling tissue comprising:
   a) an elongated cannula having a sharpened distal end;
   b) an elongated stylet having a sharpened distal end and a recess located at the distal end of said stylet, said recess located proximal to the ultimate distal end of said stylet, said recess extending transverse to the elongated axis of said stylet and extending into the body of said stylet, said stylet insertable into said cannula along a common linear axis of said stylet and said cannula, said stylet having an outer diameter slightly less than the inner diameter of said cannula, said stylet being removable from within said cannula, said stylet removable from said cannula essentially along said common linear axis whereby said stylet is also removable from said biopsy device;
   c) a cannula actuator for moving said cannula along the linear axis of said cannula;
   d) means for connecting said cannula to said cannula actuator;
   e) a stylet actuator for moving said stylet along the linear axis of said cannula for advancing said stylet into the tissue to be sampled;
   f) means for connecting said stylet to said stylet actuator;
   g) a housing having a relatively open first end for receiving both said cannula actuator and said stylet actuator therethrough and a closed second end through which said cannula slidably extends, said cannula actuator and said stylet actuator constrained within said housing to relative parallel motion along an axis parallel to the elongated axis of said cannula; and,
   h) means for selectively allowing removal of said stylet and said stylet actuator for said biopsy device,
   whereby a sample collected in said recess can be removed from said biopsy device by removing said stylet from said biopsy device while leaving said cannula in position in the tissue from which the biopsy sample is collected.

2. The biopsy device of claim 1 wherein said means for selectively allowing removal of said stylet comprises:
   a) an elongated trough in said cannula actuator having the open side of said trough directed towards said stylet actuator, said trough having a proximal end wall;
   b) a protrusion extending away from said stylet actuator toward said elongated trough in said cannula actuator; and,
   wherein said stylet actuator and said protrusion are made of a resilient material to allow said protrusion to be manually moved away from said cannula actuator when said protrusion is in contact with said proximal end wall of said trough whereby when said stylet is placed within said cannula and said cannula actuator and stylet actuator are placed within said housing and constrained within said housing to relative parallel motion, said protrusion contacts said proximal end wall of said elongated trough when said stylet actuator is moved in a proximal direction relative to said cannula actuator thereby inhibiting said stylet actuator from further movement proximal to said cannula actuator, and whereby said stylet actuator and said protrusion are manually moved away from contact with said proximal end wall of said trough so that proximal movement of said stylet actuator relative to said cannula actuator moves said protrusion over and away from said proximal end wall of said elongated trough thereby allowing said stylet to be removed from said cannula essentially along said common linear axis by further proximal movement of said stylet actuator relative to said cannula actuator.

3. A biopsy device as in claim 2 wherein said protrusion is located at the proximal end of said stylet actuator.

4. A biopsy device as in claim 3 wherein said protrusion has a gradual taper from its distal end to its proximal end in a direction away from said stylet actuator, whereby said taper facilitates reinsertion of said stylet into said cannula.

5. A biopsy device as in claim 2 wherein said protrusion is also said means for connecting said stylet to said stylet actuator.

6. A biopsy device as in claim 2 wherein said protrusion has a gradual taper from its distal end to its proximal end in a direction away from said stylet actuator, whereby said taper facilitates reinsertion of said stylet into said cannula.

7. A biopsy device as in claim 2 further comprising a narrow lip located at the proximal end of said protrusion, said lip extending away from said protrusion and said stylet actuator, whereby said lip contacts said proximal end wall of said trough.

8. A biopsy device as in claim 1 further comprising means for selectively preventing the distal movement of said stylet actuator relative to said housing when the proximal end of said stylet actuator is aligned with the proximal end of said cannula actuator when said cannula actuator is in its most proximal position.

9. A biopsy device as in claim 1 further comprising means for selectively preventing the distal motion of said cannula actuator relative to said housing when said cannula actuator is in its most proximal position.

10. A biopsy device as in claim 1 further comprising means for preventing said cannula actuator from proximal motion relative to said housing beyond a desired most proximal position.

11. A biopsy device as in claim 1 further comprising means for aligning the most proximal end of said stylet actuator with the most proximal end of said cannula actuator when said cannula actuator is in its most proximal position relative to said housing.

12. A biopsy device as in claim 1 wherein said means for selectively allowing removal of said stylet comprises:
 a) a stylet stop attached to said cannula actuator and located along said common linear axis; and,
 b) means, attached to said stylet actuator and contacting said stylet stop, for preventing proximal motion of said stylet actuator relative to said cannula actuator whereby said distal end of said cannula is prevented from being extended beyond said distal end of said stylet.

13. The biopsy device as in claim 12 wherein said stylet stop includes at least one stop lug extending outward from said stylet stop, wherein said stylet actuator includes an extension extending around at least the side of said stylet stop having said stop lug, and wherein said means for contacting said stylet stop includes at least one locking lug extending from said extension on said stylet actuator which locking lug contacts corresponding said stop lug on said stylet stop to prevent proximal motion of said stylet actuator relative to said cannula actuator.

14. The biopsy device of claim 13 wherein said stop lug is tapered from its most proximal end to its distal end in a direction of increasing thickness and wherein said locking lug is tapered from its most distal end to its most proximal end in increasing thickness and wherein said stop lug contacts said locking lug along the tapered surface of both said stop lug and said locking lug as said stylet actuator is moved distal relative to said cannula actuator whereby contact between the tapered surfaces of said stop lug and said locking lug causes said locking lug to move toward said cannula actuator, as said stylet actuator is moved distal relative to said cannula actuator, until said locking lug has moved past said stop lug whereafter said locking lug moves away from said cannula actuator so that contact between said stopping lug and locking lug constrains sad stylet actuator from proximal motion relative to said cannula actuator.

15. The biopsy device of claim 12 wherein said stylet stop is also said means for connecting said cannula to said cannula actuator.

16. A biopsy device for sampling tissue comprising:
 a) an elongated cannula having a sharpened distal end;
 b) an elongated stylet having a sharpened distal end and a recess located at the distal end of said stylet, said recess located proximal to the ultimate distal end of said stylet, said recess extending transverse to the elongated axis of said stylet and extending into the body of said stylet, said stylet insertable into said cannula along a common linear axis of said stylet and said cannula, said stylet having an outer diameter slightly less than the inner diameter of said cannula, said stylet being removable from within said cannula, said stylet removable from said cannula essentially along said common linear axis whereby said stylet is also removable from said biopsy device;
 c) a cannula actuator for moving said cannula along the linear axis of said cannula;
 d) means for connecting said cannula to said cannula actuator;
 e) a stylet actuator for moving said stylet along the linear axis of said cannula for advancing said stylet into the tissue to be sampled, said stylet actuator made of a resilient material so that said stylet actuator may be manually moved away from said cannula actuator;
 f) means for connecting said stylet to said stylet actuator;
 g) a housing having a relatively open first end for receiving both said cannula actuator and said stylet actuator therethrough and a closed second end through which said cannula slidably extends, said cannula actuator and said stylet actuator constrained within said housing to relative parallel motion along an axis parallel to the elongated axis of said cannula; and, h) means for selectively allowing removal of said stylet and said stylet actuator from said biopsy device comprising:
  i) an elongated trough in said cannula actuator having the open side of said trough directed towards said stylet actuator, said trough having a proximal end wall;
  ii) a protrusion extending away from said stylet actuator toward said elongated trough in said cannula actuator, said protrusion having a gradual taper from its distal end to its proximal end in a direction away from said stylet actuator, said protrusion having a narrow lip located at the proximal end of said protrusion, said lip extending away from the gradual taper of said protrusion, said protrusion being also said means for connecting said stylet to said stylet actuator, whereby said taper facilitates reinsertion of said stylet into said cannula, so that when said stylet is placed within said cannula and said cannula actuator and stylet actuator are placed within said housing and constrained within said housing to relative parallel motion, said narrow lip contacts said proximal end wall of said elongated trough when said stylet actuator is moved in a proximal direction relative to said cannula actuator thereby inhibiting said stylet actuator from further movement proximal to said cannula actuator, and whereby movement of said stylet actuator away from said cannula actuator moves said narrow lip and said protrusion clear of said proximal end wall of said elongated trough thereby allowing said stylet to be removed from said cannula essentially along said common linear axis by further proximal movement of said stylet actuator relative to said cannula actuator;

whereby a sample collected in said recess can be removed from said biopsy device by removing said stylet from said biopsy device while leaving said cannula in position in the tissue from which the biopsy sample is collected, said stylet removable from said biopsy device by moving said lip away from said proximal end wall while moving said stylet actuator proximally to said cannula actuator so that said lip and said protrusion moves proximally past said proximal end wall thereby allowing said stylet to be removed from said cannula and said biopsy device along essentially said common linear axis.

17. A biopsy device for sampling tissue comprising:
a) an elongated cannula having a sharpened distal end;
b) an elongated stylet having a sharpened distal end and a recess located at the distal end of said stylet, said recess located proximal to the ultimate distal end of said stylet, said recess extending transverse to the elongated axis of said stylet and extending into the body of said stylet, said stylet insertable into said cannula along a common linear axis of said stylet and said cannula, said stylet having an outer diameter slightly less than the inner diameter of said cannula, said stylet being removable from within said cannula, said stylet removable from said cannula essentially along said common linear axis whereby said stylet is also removable from said biopsy device;
c) a cannula actuator for moving said cannula along the linear axis of said cannula;
d) means for connecting said cannula to said cannula actuator;
e) a stylet actuator for moving said stylet along the linear axis of said cannula for advancing said stylet into the tissue to be sampled;
f) means for connecting said stylet to said stylet actuator;
g) a housing having a relatively open first end for receiving both said cannula actuator and said stylet actuator therethrough and a closed second end through which said cannula slidably extends, said cannula actuator and said stylet actuator constrained within said housing to relative parallel motion along an axis parallel to the elongated axis of said cannula; and,
h) means for selectively allowing removal of said stylet and said stylet actuator from said biopsy device comprising:
  i) a stylet stop attached to said cannula actuator and located along said common linear axis, said stylet stop including at least one stop lug extending outward from said stylet stop, said stop lug being tapered from its most proximal end to its distal end in a direction of increasing thickness, said stylet stop being also said means for connecting said cannula to said cannula actuator;
  ii) means, attached to said stylet actuator, for contacting said stylet stop to prevent proximal motion of said stylet actuator relative to said cannula actuator whereby said cannula is prevented from being extended beyond said distal end of said stylet, said means comprising:
    1) an extension of said stylet actuator extending around at least the side of said stylet stop having said stop lug;
    2) at least one locking lug extending from said extension of said stylet actuator, said locking lug adapted to contact corresponding said stop lug on said stylet stop to prevent proximal motion of said stylet actuator relative to said cannula actuator, said locking lug being tapered from its most distal end to its most proximal end in increasing thickness;

whereby said stop lug contacts said locking lug along the tapered surface of both said stop lug and said locking lug as said stylet actuator is moved distally relative to said cannula actuator, and whereby contact between the tapered surfaces of said stop lug and said locking lug causes said locking lug to move toward said cannula actuator, as said stylet actuator is moved distally relative to said cannula actuator, until said locking lug has moved past said stop lug whereafter said locking lug moves away from said cannula actuator so that said stop lug and said locking lug no longer contact each other along their respective tapered surfaces whereby contact between said stopping lug and locking lug constrains said stylet actuator from proximal motion relative to said cannula actuator, and, whereby a sample collected in said recess can be removed from said biopsy device by removing said stylet from said biopsy device while leaving said cannula in position in the tissue from which the biopsy sample is collected, said stylet removable from said biopsy device by manually moving said locking lug toward said cannula actuator while moving said stylet actuator proximally to said cannula actuator so that said locking lug moves proximally past said stop lug thereby allowing said stylet to be removed from said cannula and said biopsy device along essentially said common linear axis.

* * * * *